(12) United States Patent
Sasaki et al.

(10) Patent No.: US 7,855,067 B2
(45) Date of Patent: Dec. 21, 2010

(54) MICROINJECTION EQUIPMENT

(75) Inventors: Jun Sasaki, Kawasaki (JP); Akihiko Yabuki, Kawasaki (JP); Shusaku Nishiyama, Kawasaki (JP); Ikushi Takasaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1038 days.

(21) Appl. No.: 11/600,810

(22) Filed: Nov. 17, 2006

(65) Prior Publication Data

US 2008/0102516 A1  May 1, 2008

(30) Foreign Application Priority Data

Jul. 4, 2006  (JP)  ............... 2006-184550

(51) Int. Cl.
C12M 3/00 (2006.01)
C12M 1/26 (2006.01)
C12M 1/36 (2006.01)

(52) U.S. Cl. .............. 435/285.1; 435/286.2; 435/287.3; 422/63; 422/100

(58) Field of Classification Search .............. 435/285.1, 435/286.2, 287.3; 422/63, 100
See application file for complete search history.

(56) References Cited

U.S. PATENT DOCUMENTS 5,639,425 A * 6/1997 Komiyama et al. ........... 422/63

OTHER PUBLICATIONS

Saya Ito, "Microinjection", Laboratory of Nuclear Signaling TCMB, University of Tokyo, Cell Science, vol. No. 3, No. 3, pp. 254-257; vol. 6, No. 4, pp. 332-335; and vol. 6, No. 5, pp. 413-416 (1990). (English translation pp. 1-7).
Mikako Saito, "Nanoinjection into ES Cell with a Single-Cell Manipulation Supporting Robot", Japan Nanonet Bulletin, vol. 81, (2 pgs.) (English Translation pp. 8-10), Jan. 26, 2006.
Microinjection with an English Translation, Whole Document.
Nanoinjection into ES Cell with a Single-Cell Manipulation Supporting Robot with English Translation, Whole Document.

* cited by examiner

*Primary Examiner*—William H Beisner
(74) *Attorney, Agent, or Firm*—Fujitsu Patent Center

(57) ABSTRACT

To provide a microinjection equipment capable of fitting a micro needle to a manipulator etc. manipulating the micro needle in short time on the occasion of an injection operation. Included are a micro needle transporting device 12 detachably grasping a micro needle 10 filled with an introduction substance and disposed in a predetermined standby position and transporting the micro needle 10 to a predetermined ready-for-introducing position, a manipulator 14 grasping in the attachable/detachable manner the micro needle 10 disposed in the predetermined ready-for-introducing position and inserting and removing the tip of the micro needle 10 into and from an introduction target micro body 13, and an introduction substance discharging device 15 discharging the introduction substance in the micro needle 10 by applying a predetermined pressure to an interior of the micro needle 10 grasped by the manipulator 14.

10 Claims, 10 Drawing Sheets

MICROINJECTION EQUIPMENT

BACKGROUND OF THE INVENTION

1. Field of the Invention

The present invention relates generally to a microinjection equipment, and more particularly to a microinjection equipment suited to a microinjection technology of introducing a gene solution, a pharmaceutical solution, etc., into a fine particle such as a cell by use of a micro needle and to a fine particle transporting technology in a biological field such as a cell analysis.

2. Description of the Related Technology

Fields such as regenerative medical treatments and developments of new drugs employ a substance introducing technology of introducing a predetermined substance into a cell and verifying whether there is an effect or not.

The conventional substance introduction technologies are represented by a virus vector method and a Lipofection method. In these methods, the whole of introduction target cells and should-be-introduced substance is treated as one batch. This type of substance introduction method is called a batchwise substance introduction method.

This batchwise substance introduction method is simple in terms of operation and uses, while on the other hand, a large quantity of cells and a large quantity of introduction substance are required for one introduction experiment. Accordingly, the batchwise substance introduction method is unsuited to a case of using precious cells and reagents. Hence, such a problem arises that the batchwise substance introduction method can not be applied to the verification of the effect provided by introducing a microdose of pharmaceutical, which will be requested from now on.

On the other hand, it is considered that a large number of patterns of experiments will hereafter be conducted by employing the microdose of cells and the introduction liquid. With such a background, there is demanded a technology of surely introducing a fixed quantity of introduction substance into the individual particles such as the cells that are as large in quantity as $10^5$ to $10^6$ pieces aseptically in a short period of time.

Such being the case, a microinjection method is proposed as a technology capable of introducing the fixed quantity of introduction substance into the individual cells (for example, see Non-Patent documents 1-3). This microinjection method is generally utilized in the field of artificial inseminations etc.

Further, there has hitherto been proposed a microinjection equipment that introduces the introduction substance into the individual cells by the microinjection method.

The microinjection equipment is constructed so that a micro needle is manipulated by a manipulator, and the introduction substance filled into an interior of the micro needle is introduced into the particle such as the cell.

[Non-Patent document 1] Saya Ito, Microinjection, [online], [searched on Apr. 14, 2006], Intenet<URL:http://www.iam.u-tokyo.ac.jp/bnsikato/protocol/7-3.html>

[Non-Patent document 2] Mikako Saito, Nano-Injection into ES Cell by Use of Single Cell Manipulation Supporting Robot, [online], [searched on Apr. 14, 2006], Internet<URL:http://www.nanonet.go.jp/japanese/mailmag/2005/081b.html>

In the conventional microinjection equipment, however, the micro needle has been manually fitted to the manipulator. Therefore, such a problem exists that a comparatively long period of time is required for fitting and exchanging the micro needle.

Moreover, in the conventional microinjection equipment, when fitting the micro needle to the manipulator, a hand and a finger might touch a needle tip, and the needle tip might be damaged and contaminated.

SUMMARY OF THE INVENTION

It is an object of the present invention, which was devised in view of the problems described above, to provide a microinjection equipment capable of fitting the micro needle to the manipulator etc. in a short period of time thereby to suppress damaging and contaminating the micro needle.

The present invention adopts the following device in order to solve the problems. The present invention is a microinjection equipment introducing an introduction substance, filled into an interior of a micro needle, into an introduction target micro body, comprising:

micro needle transporting device detachably grasping the micro needle filled with the introduction substance and disposed in a predetermined standby position, and transporting the micro needle to a predetermined ready-for-introducing position; micro needle inserting/removing device detachably grasping the micro needle disposed in the predetermined ready-for-introducing position, and inserting and removing the tip of the micro needle into and from the introduction target micro body; and introduction substance discharging device discharging the introduction substance from the micro needle by applying a predetermined pressure to the introduction substance within the micro needle grasped by the micro needle inserting/removing device.

A glass tube of the micro needle can be exemplified by a glass tube that is having an outer diameter on the order of 1.0 mm-1.2 mm and an inner diameter on the order of 0.5 mm-0.7 mm, wherein the needle tip having an outer diameter on the order of 1 μm and an inner diameter on the order of 0.5 μm.

Further, the micro needle inserting/removing device can be exemplified by a manipulator etc. that moves the micro needle in an X-axis direction and in a Y-axis direction that are orthogonal to each other and in a direction oblique to the horizontal direction. Moreover, the introduction target micro body can be exemplified by a cell.

According to the present invention, the micro needle transporting device transports the micro needle filled with the introduction substance and disposed in the predetermined standby position to the predetermined ready-for-introducing position. Next, the micro needle inserting/removing device inserts the tip of the micro needle into the introduction target micro body, and the introduction substance discharging device introduces the introduction substance into the introduction target micro body by applying a pressure to the introduction substance in the micro needle. Thus, according to the present invention, it is possible to automatically perform the operations starting with transporting the micro needle disposed in the standby position and ending with introducing the introduction substance into the introduction target micro body.

It is therefore feasible to fit and exchange in the short time the micro needle with respect to the micro needle inserting/removing device such as the manipulator. Further, neither the hand nor the finger touches the micro needle, and hence damaging and contaminating the micro needle can be suppressed.

Herein, it is possible to take such a configuration that the micro needle has a cap for protecting the needle tip, and the micro needle transporting device grasps the cap.

According to this configuration, the cap is grasped by the micro needle transporting device, and the micro needle is grasped by the micro needle inserting/removing device, in which state the micro needle transporting device is moved in a direction of away from the micro needle inserting/removing device, thereby enabling the cap to be easily removed from the micro needle.

Still further, such a configuration can be taken that the micro needle includes a hollowed glass tube and a holder having a first holding member that holds an intermediate portion of the hollowed glass tube and a second holing member that holds a proximal portion of the hollowed glass tube.

According to this configuration, the two portions, i.e., the proximal portion and the intermediate portion of the glass tube can be held by the holder, whereby the glass tube can be stably held.

Yet further, a configuration can be adopted, wherein the introduction substance discharging device has a tube that applies a pressure to the introduction substance in the micro needle, and the holder has a guide hole that guides the tube into the micro needle.

This configuration enables the tube to be surely inserted into the micro needle. Accordingly, the introduction substance in the micro needle can be surely discharged.

There can be taken such a configuration that the micro needle inserting/removing device includes a central-axis line directional positioning device that positions the micro needle in a direction of the central-axis line, and an orthogonal direction positioning device that positions the micro needle in a direction orthogonal to the central-axis line.

With this configuration, the micro needle can be held always in the same position, and hence, on the occasion of exchanging the micro needle, there is no necessity of adjusting the fitting position of the micro needle.

EFFECTS OF THE INVENTION

According to the present invention, it is possible to automatically perform a series of operations starting with transporting the micro needle filled with the introduction substance and disposed in the predetermined standby position to the predetermined ready-for-introducing position by the micro needle transporting device, then inserting the tip of the micro needle into the introduction target micro body in a way that grasps this micro needle by the micro needle inserting/removing device, and ending with introducing the introduction substance in the micro needle into the introduction target micro body by the introduction discharging device.

Accordingly, the micro needle can be fitted (grasped) in the short time to the micro needle inserting/removing device, so that operation efficiency can be increased. Moreover, neither the hand nor the finger touches the micro needle during the operation, and hence damaging and contaminating the micro needle can be suppressed.

DETAILED DESCRIPTION OF THE INVENTION

A microinjection equipment according to the present invention will hereinafter be described in detail with reference to the drawings.

Figure 1:
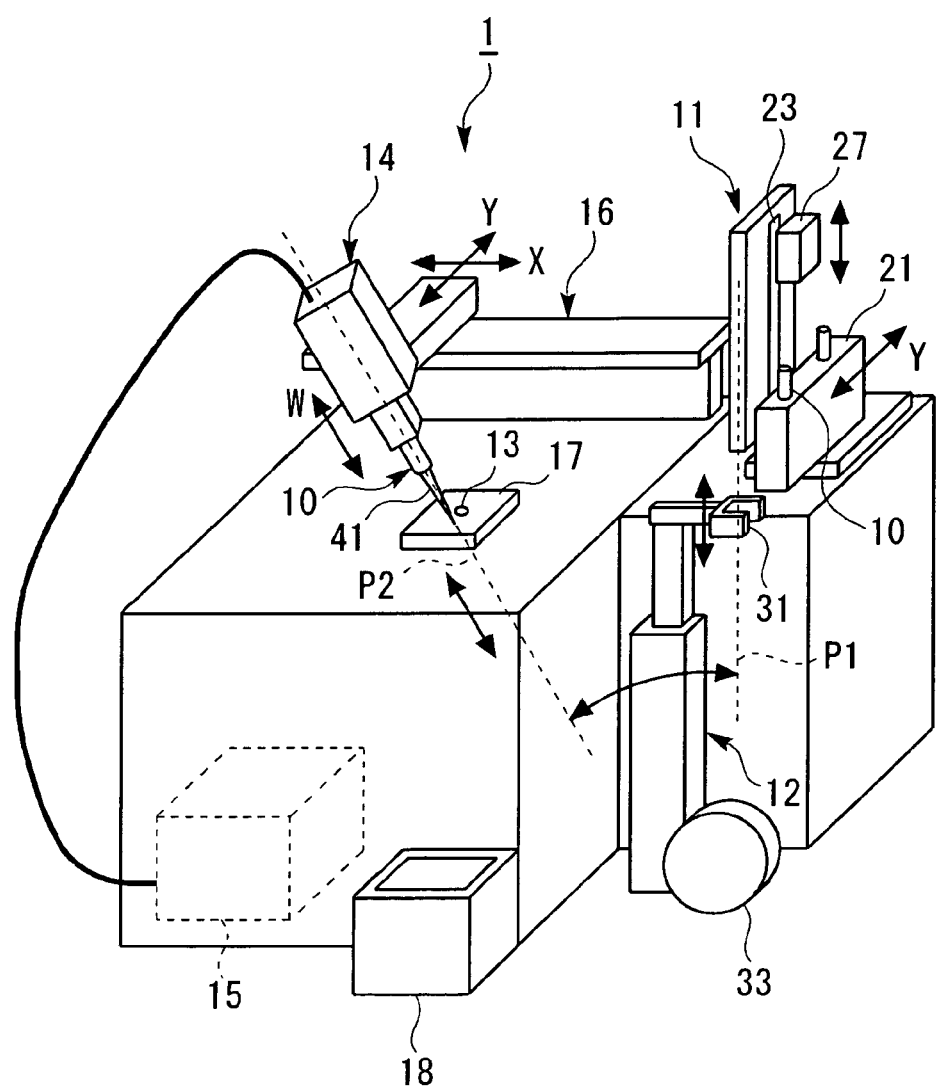
FIG. 1 is a perspective view showing a microinjection equipment according to the present invention.

FIG. 1 shows a microinjection equipment 1 in an embodiment according to the present invention. This microinjection equipment 1 is constructed so that an introduction substance, with which an interior of a micro needle 10 is filled, is automatically introduced into a piece of introduction target micro body 13.

Namely, this microinjection equipment 1 includes an introduction substance filling device 11 that fills the interior of the micro needle 10 with the introduction substance and disposes the micro needle 10 in a predetermined standby position, a micro needle transporting device 12 that detachable grasps the micro needle 10 disposed in the predetermined standby position and transports this micro needle 10 to a predetermined ready-for-introducing position, a manipulator 14 defined as a micro needle inserting/removing device that inserts and removes a tip of the micro needle 10 into and from the introduction target micro body 13 by grasping in the attachable/detachable manner the micro needle 10 disposed in the predetermined ready-for-introducing position, and an introduction substance discharging device 15 that discharges the introduction substance from within the micro needle 10 by applying a predetermined pressure to the introduction substance in the micro needle 10 grasped by this manipulator 14.

Figure 2:
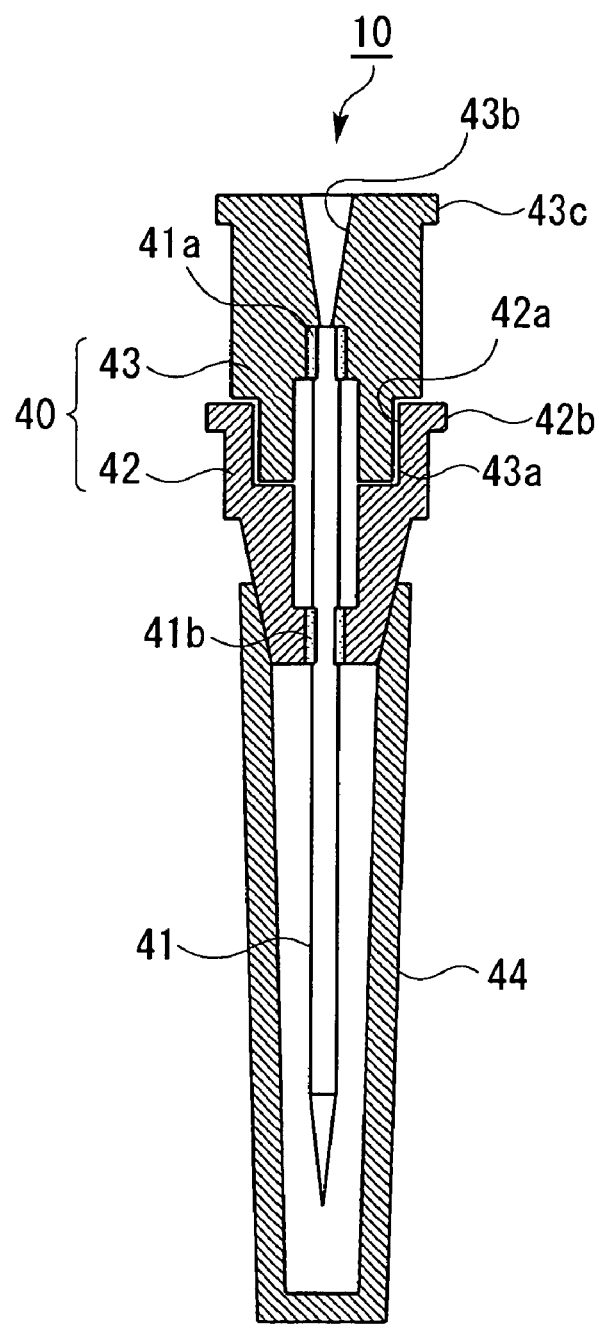
FIG. 2 is a sectional view showing a micro needle according to the present invention.

Next, the respective components will be explained. The micro needle 10 has, as shown in FIG. 2, an extra-fine glass tube 41 and a holder 40 that holds this glass tube 41.

The glass tube 41 is hollowed having an outer diameter on the order of 1.0 mm-1.2 mm and an inner diameter on the under of 0.5 mm-0.7 mm. Further, the tip of the glass tube 41 is formed at an acute angle. The tip of the glass tube 41 is formed having an outer diameter on the order of 1 µm and an inner diameter on the order of 0.5 µm.

The holder 40 includes a first holding member 42 that holds an intermediate portion 41b of the glass tube 41, and a second holding member 43 that holds a proximal portion 41a of the glass tube 41. A cap 44 for protecting the glass tube 41 is detachably attached to the first holding member 42. The cap 44 is formed in a tapered shape.

The first holding member 42 and the second holding member 43 are respectively provided with a recessed portion 42a and a protruded portion 43a in their face-to-face areas. The recessed portion 42a and the protruded portion 43a are fitted together, whereby the first holding member 42 and the second holding member 43 are connected to each other.

The first holding member 42 is formed in a cylindrical shape substantially in one half and in a funnel shape in the other half. The proximal portion 41a of the glass tube 41 and is inserted into by passing through the first holding member 42. The intermediate portion 41b of the glass tube 41 is bonded to and thus held by a forward end portion of the first holding member 42. One end of the first holding member 42 is provided with a flange 42b.

The second holding member 43 is formed in the cylindrical shape. The proximal portion 41a of the glass tube 41 is inserted up to an intermediate portion in the second holding member 43. The proximal portion 41a of the glass tube 41 is bonded to and is thus held by the second holding member 43.

Further, the second holding member 43 is provided with a guide hole 43b continuous to a through-hole 41c (see FIG. 9) of the glass tube 41. This guide hole 43b is formed in a tapered shape gradually expanding toward the outside from the side of the glass tube 41. One end of the second holding member 43 is provided with a flange 43c.

A gene solution and a pharmaceutical solution can be exemplified as the introduction substance with which the interior of the micro needle 10 is filled. Further, a cell and a variety of particles similar to the cell can be exemplified as the introduction target micro body 13.

Figure 3:
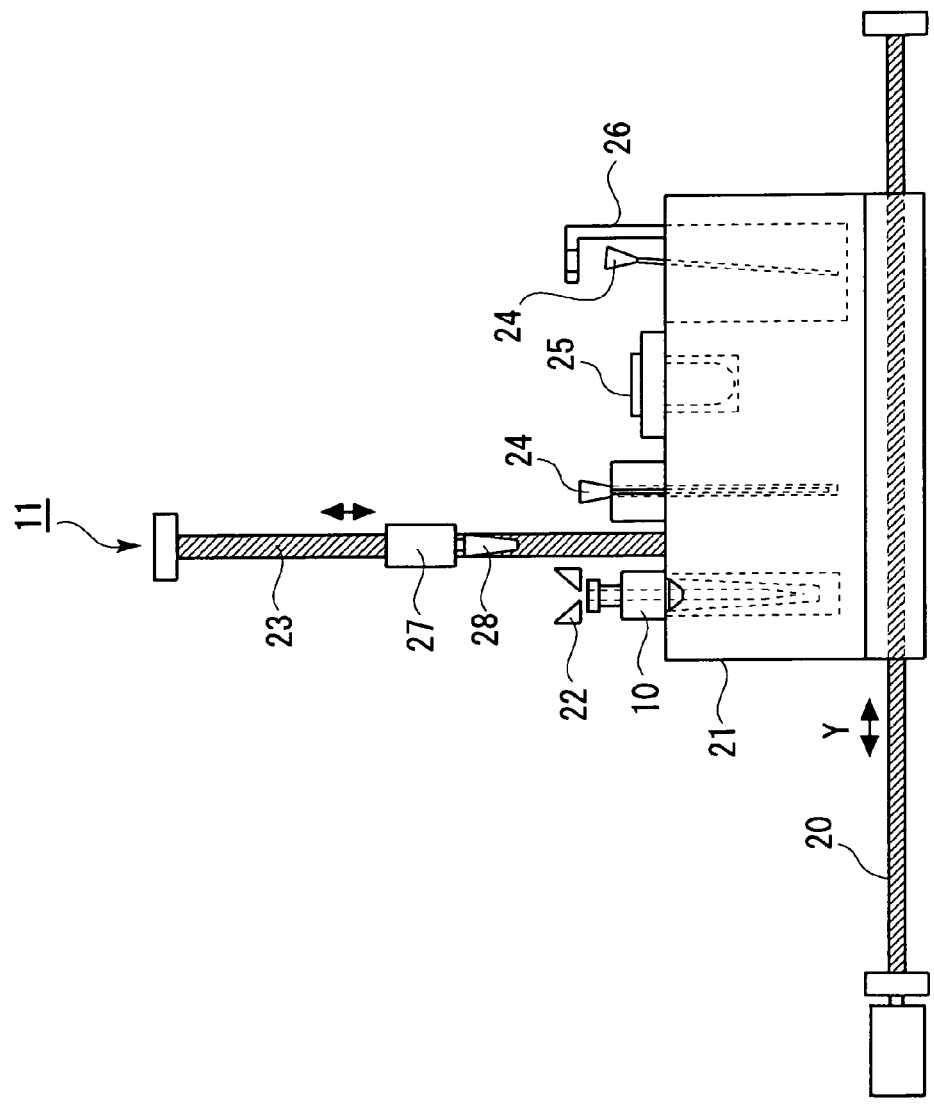
FIG. 3 is a diagram showing an introduction substance filling device according to the present invention.

The introduction substance filling device 11 has, as illustrated in FIG. 3, a cartridge 21 movable in a predetermined direction Y, a cartridge moving mechanism 20 for moving this cartridge 21, an insertion tube guide mechanism 22 and an insertion tube up-and-down moving mechanism 23, both of which are disposed above the cartridge 21.

The cartridge 21 is provided with a magazine for supplying the micro needle 10, a magazine for supplying an insertion tube 24, a magazine for supplying a solution containing receptacle 25 containing the solution that should be filled into interior of the micro needle 10, and an insertion tube removing member 26.

Figure 4:
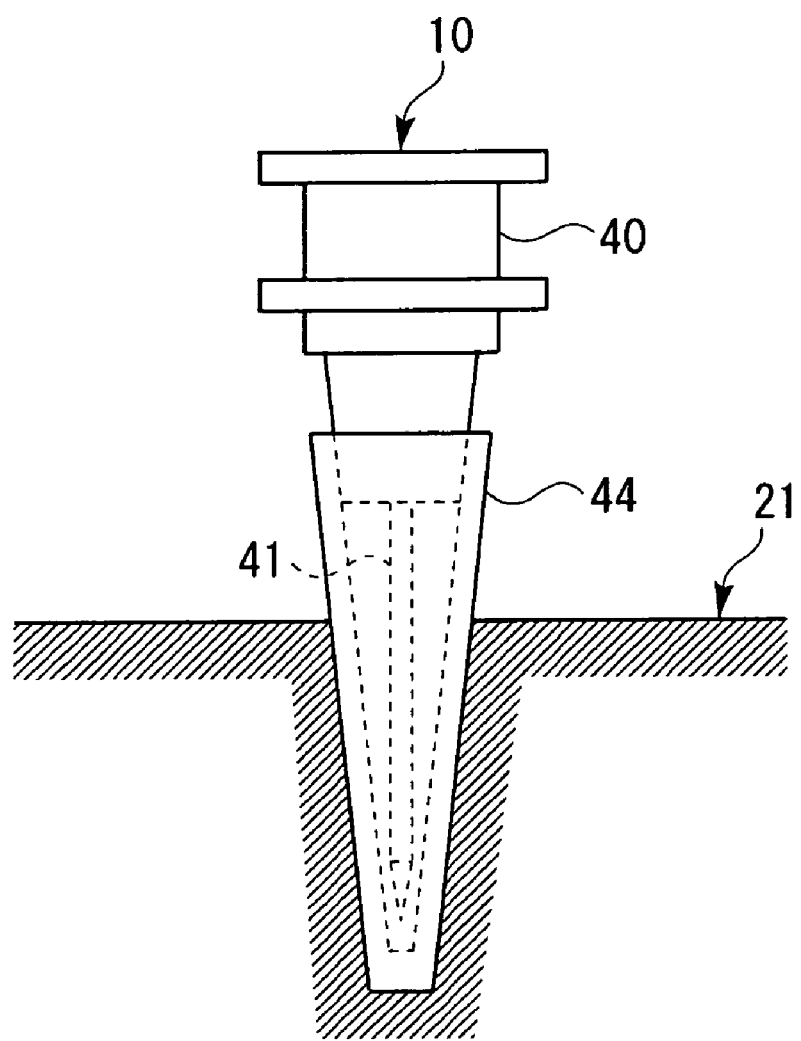
FIG. 4 is a diagram showing the micro needle accommodated in a cartridge according to the present invention.

In a state where the micro needle 10 is held by the cartridge 21, as shown in FIG. 4, an upper portion of the cap 44 and the holder 40 are protruded above from the cartridge 21. Further, an appropriately wide space is provided along the periphery of the upper portion of each of the holder 40 and the cap 44. Thus, as will be explained later, the upper portion of the cap 44 protruding from the cartridge 21 can be grasped by a hand 31 of the micro needle transporting device 12.

Further, the insertion tube up-and-down moving mechanism 23 is provided with a liquid control pump 27 which is vertically movable. This liquid control pump 27 includes an insertion tube connecting member 28.

In this introduction substance filling device 11, at first, the respective magazines for the micro needle 10, the insertion tube 24 and the solution containing receptacle 25 and also the insertion tube removing member 26 are mounted in magazines provided on the cartridge 21.

Next, the cartridge 21 is moved horizontally, and the insertion tube 24 is connected to the liquid control pump 27 through the insertion tube connecting member 28. Subsequently, the cartridge 21 is moved horizontally in the direction Y, and the tip of the insertion tube 24 is inserted into the solution containing receptacle 25. Then, a solution in the solution containing receptacle 25 is sucked by the liquid control pump 27.

Next, the liquid control pump 27 and the insertion tube 24 are ascended, while the cartridge 21 is moved horizontally. Subsequently, the insertion tube 24 is inserted into the micro needle 10. Next, the introduction substance in the liquid control pump 27 is ejected into the micro needle 10. The introduction substance is thereby filled into the micro needle 10.

Next, the liquid control pump 27 is ascended, and the insertion tube 24 is moved to above the micro needle 10. Subsequently, the cartridge 21 is moved horizontally, and the insertion tube 24 is moved to the insertion tube removing member 26. Next, the insertion tube 24 connected to the liquid control pump 27 is removed by the insertion tube removing member 26.

Thus, after filling the micro needle 10 with the introduction substance, the cartridge 21 is moved in the direction Y, and the micro needle 10 is disposed in a predetermined standby position P1. Namely, the cartridge 21 functions as a standby position disposing device that disposes the micro needle 10 filled with the introduction substance in the predetermined standby position P1.

Figure 5:
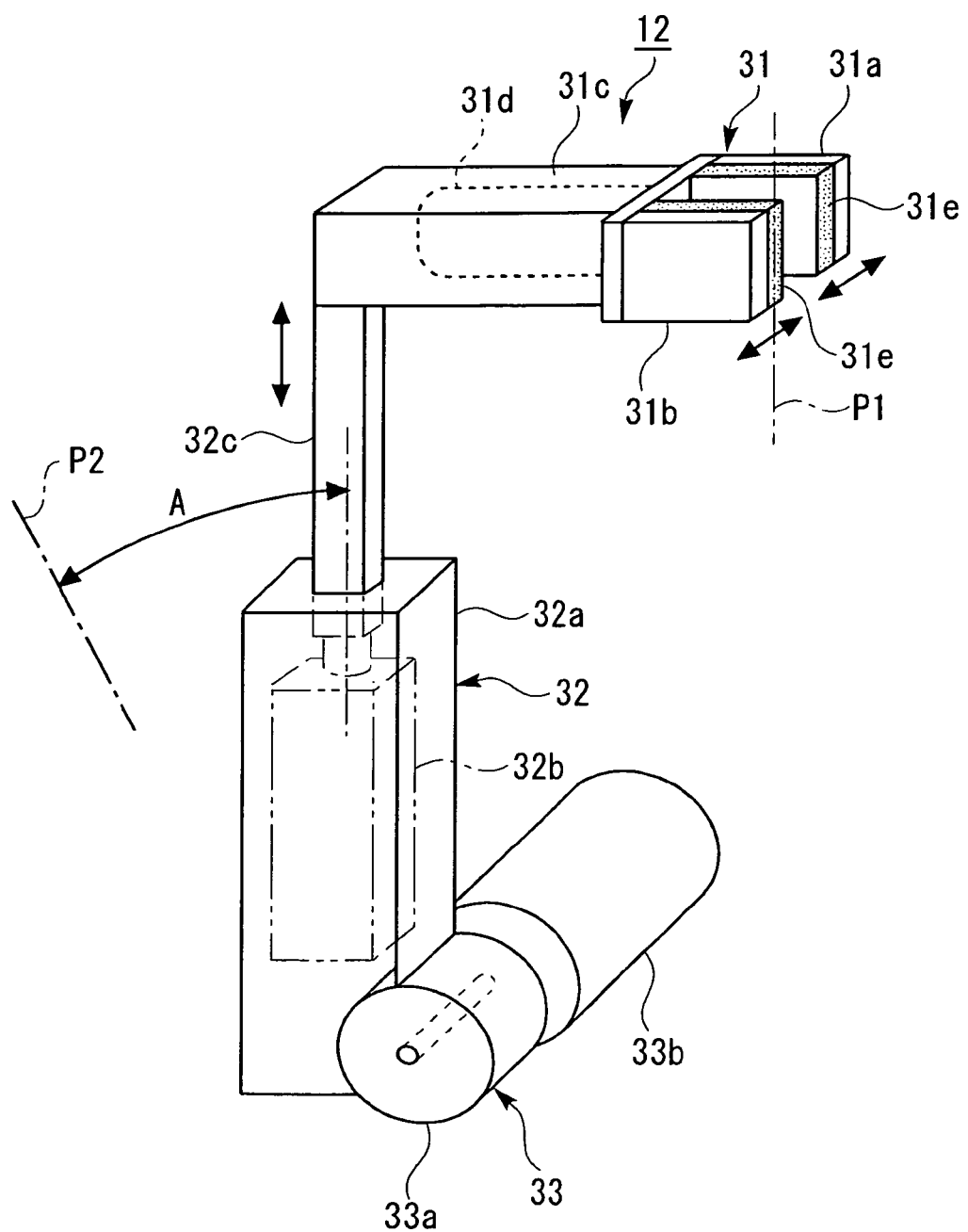
FIG. 5 is a perspective view showing a micro needle transporting device according to the present invention.

The micro needle transporting device 12 in FIG. 1, in as shown in FIG. 5, detachable grasping the micro needle 10 disposed in the predetermined standby position P1, and transporting the micro needle 10 to a predetermined ready-for-introducing position P2.

This micro need transporting device 12 includes the hand 31 for grasping the micro needle 10, an up-and-down moving unit 32 that moves this hand 31 up and down, and a turning unit 33 that turns the up-and-down moving unit 32 through a predetermined angle in a predetermined turning direction A.

The hand 31 has two pieces of plate members 31a, 31b disposed in parallel, an arm 31c that holds these plate members 31a, 31b, and a driving unit 31d such as a motor and a cylinder for opening and closing the plate members 31a, 31b. Moreover, a flexible buffer material 31e is provided on inner surfaces of the plate members 31a, 31b.

Figure 6A:
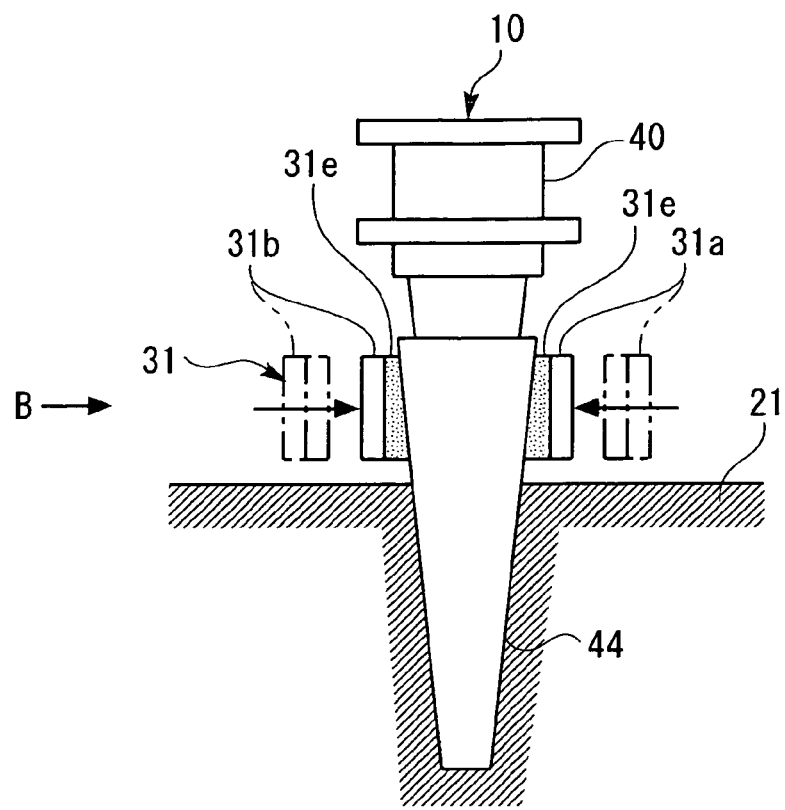
FIG. 6A is a view showing a state where the micro needle accommodated in the cartridge according to the present invention is grasped by a hand of the micro needle transporting device.
Figure 6B:
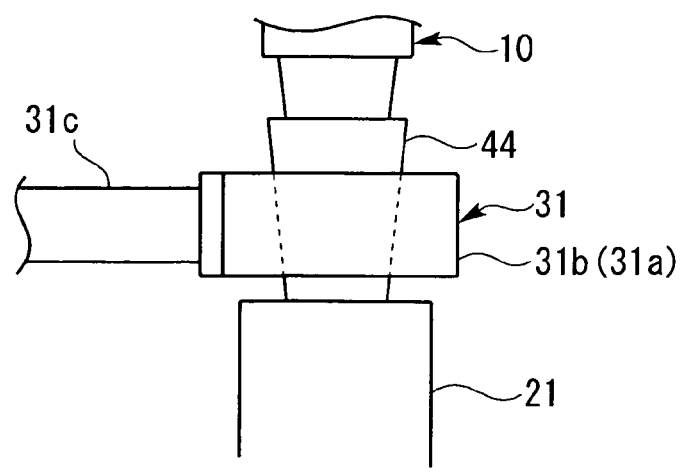
FIG. 6B is a view taken along an arrowed line in FIG. 6A.

When the hand 31 grasps the micro needle 10 in the cartridge 21, as illustrated in FIGS. 6(A) and 6(B), the plate members 31a, 31b are opened and are disposed on both sides of the cap 44 on the cartridge 21. Next, the plate members 31a, 31b are closed to grasp the cap 44, namely the micro needle 10. At this time, the buffer material 31e deforms along the tapered cap 44. With this operation, an uniform grasping force acts on the cap 44.

The up-and-down moving unit 32 in FIG. 5 includes a base 32a and a cylinder 32b provided in the base 32a. A rod 32c is secured to a piston of this cylinder 32b. An upper end of the rod 32c is fitted with the hand 31. The piston of the cylinder 32b extends and retracts, whereby the hand 31 is moved up and down.

The turning unit 33 is provided at a lower end portion of the up-and-down moving unit 32. This turning unit 33 includes a rotary drum 33a and a motor 33b that rotates the rotary drum 33a in both diameters. The base 32a of the up-and-down moving unit 32 is secured to the rotary drum 33a.

The rotation of the rotary drum 33a turns the up-and-down moving unit 32 to a predetermined turning position substantially from a perpendicular direction. The micro needle 10 grasped by the hand 31 is thereby transported to the predetermined ready-for-introducing position (P2) from the predetermined standby position (P1). Note that a rotational angle of the rotary drum 33a can be arbitrarily adjusted.

Figure 7:
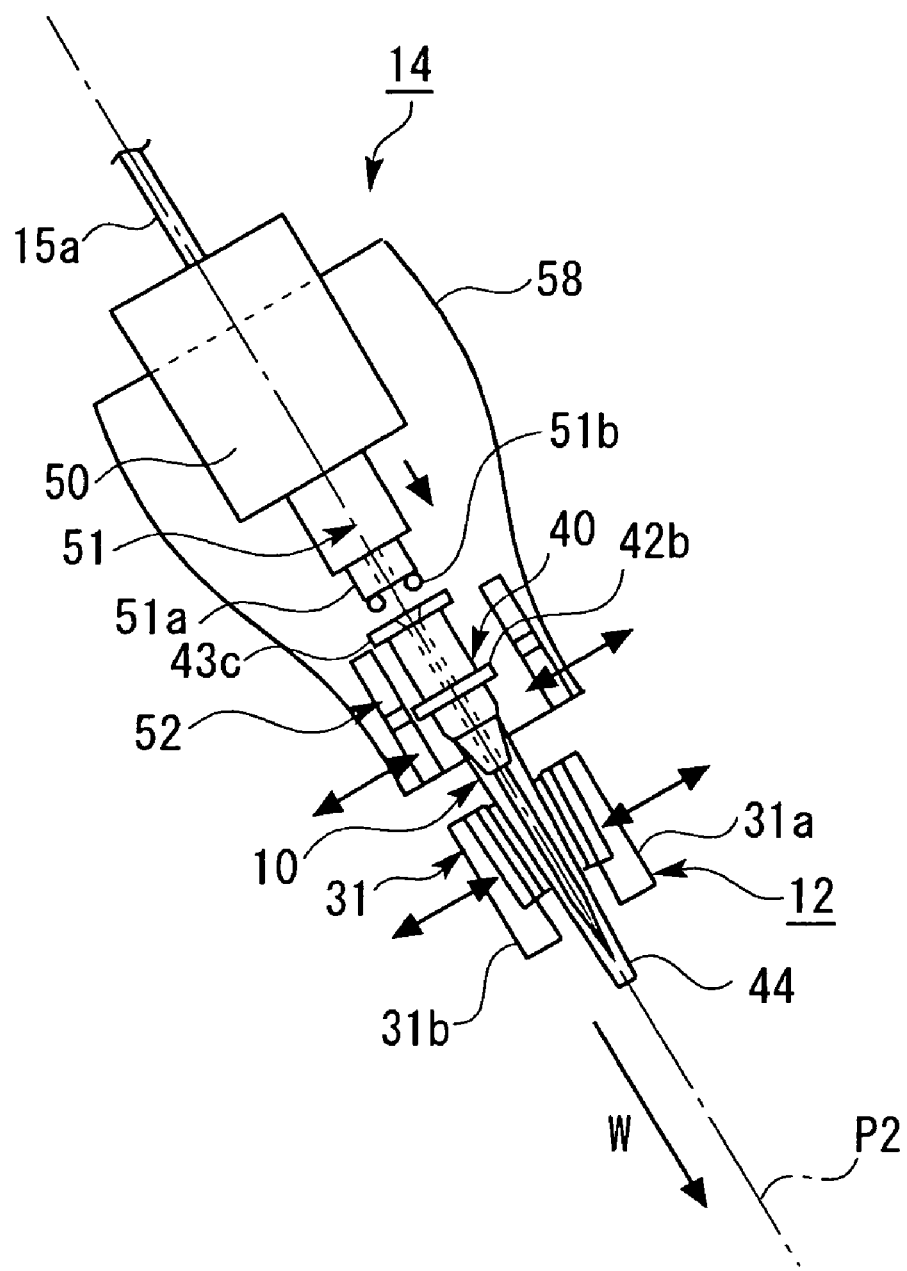
FIG. 7 is a view showing a state where the micro needle is grasped by a micro needle inserting/removing device according to the present invention.

The manipulator 14 in FIG. 1 has, as shown in FIG. 7, a main body 50, a connecting member 51 provided at a forward end of this main body 50, and a hand 52 that detachable grasps the micro needle 10 disposed in the predetermined ready-for-introducing position P2. Note that the numeral 16 in FIG. 7 represents an X-Y stage for moving the manipulator 14 in the direction X and in the direction Y that are orthogonal to each other.

The main body 50 and the hand 52 are formed as separate units but are secured to a same base plate 58. Further, the connecting member 51 includes a small-diameter portion 51a and an O-ring 51b provided at a forward end of this small-diameter portion 51a.

The connecting member 51 is slidably moved by a cylinder provided in the main body 50 in such directions as to close to and get away from the micro needle 10 grasped by the hand 52. The connecting member 51 moves toward the micro needle 10, whereby the O-ring 51b of the forward end of the connecting member 51 is pressed against an edge surface of the flange 43c in the holder 40 for the micro needle 10 grasped by the hand 52. With this operation, the O-ring 51b is crushed, thereby keeping hermetic seal between the micro needle 10 and the connecting member 51.

Figure 8:
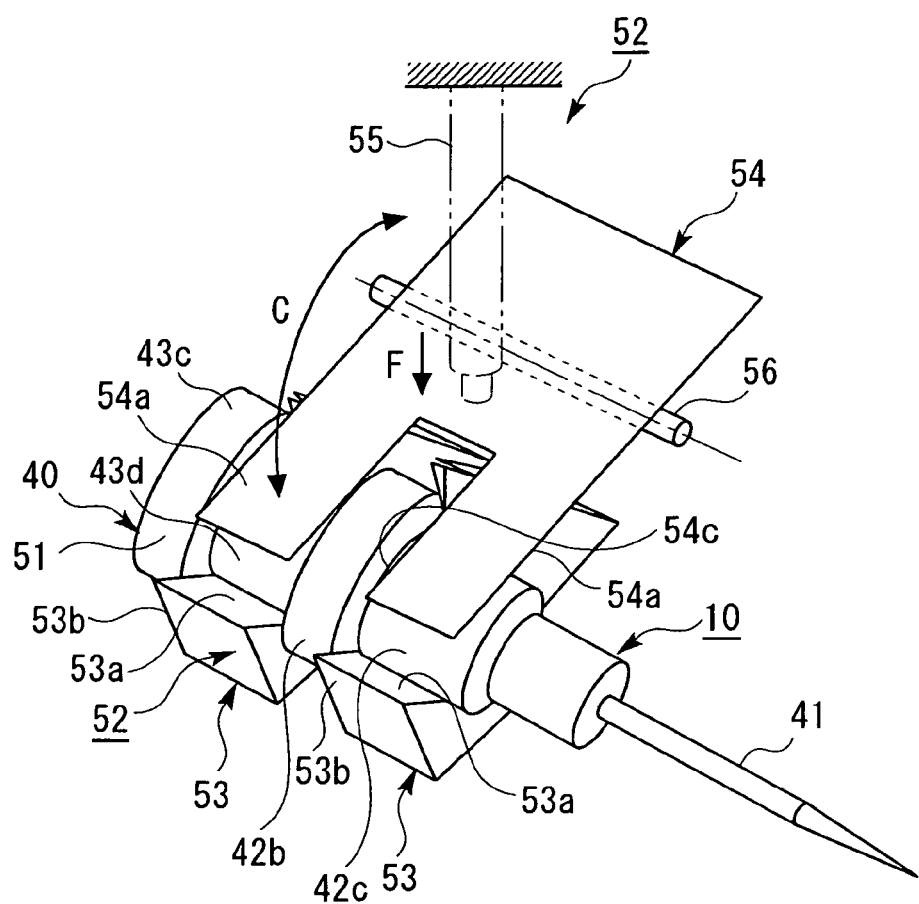
FIG. 8 is a perspective view showing a hand of the micro needle inserting/removing device.

The hand 52 includes, as illustrated in FIG. 8, a pair of support portions 53, 53 for supporting partial areas of an outer peripheral surface of the holder 40 holding the micro needle 10, a presser plate 54 that presses the holder 40 from the side opposite to the support portion 53, and a cylinder 55 that applies a pressing force F to the presser plate 54.

The support portions 53, 53 are formed with V-grooves 53a, 53a, respectively. The pair of V-grooves 53a, 53a serves to support partial areas of outer peripheral surfaces 42c, 43d of the first holding member 42 and of the second holding member 43. It is to be noted that the flange 42b of the holder 40 is inserted into a gap between the support portions 53, 53.

The presser plate 54 has a pair of presser pieces 54a, 54a abutting on the outer peripheral surfaces 42c, 43d in the holder 40. A notch 54c for steering clear of the flange 42b is formed between the presser pieces 54a, 54a. Further, an intermediate portion of the presser plate 54 is provided with a rotary shaft 56 substantially parallel to the central-axis line of the micro needle 10.

This presser plate 54 is turned by rotations of the rotary shaft 56 in directions C to close to and away from the micro needle 10.

The micro needle 10 grasped by the hand 52 is pressed by the connecting member 51 of the manipulator 14 in the direction of the central-axis line. With this operation, the flange 42b of the first holding member 42 at the flange 43c of the second holding member 43 are pressed against side surfaces (support surfaces) 53b, 53b of the support portions 53, 53. Thereby, positioning of the micro needle 10 in the direction of the central-axis line is performed.

Namely, the main body 50 of the manipulator 14 and the side surfaces 53b, 53b of the support portions 53, 53 in the hand 52 constitute a central-axis line directional positioning device for the micro needle 10.

Moreover, the outer peripheral surfaces 42c, 43d of the holder 40 are pressed against the inner surfaces of the V-grooves 53a, 53a by the presser plate 54. The micro needle 10 is thereby positioned in an orthogonal direction orthogonal to the direction of the central-axis line of the micro needle 10.

Namely, the V-grooves 53a, 53a, the presser plate 54 and the cylinder 55 constitute an orthogonal direction positioning device in the direction orthogonal to the central-axis line of the micro needle 10.

As shown in FIG. 7, after the micro needle 10 has been grasped by the hand 52 of the manipulator 14, the hand 31 of the micro needle transporting device 12 moves back in a direction W to be away from the micro needle 10 while grasping the cap 44. With this operation, the cap 44 is removed from the micro needle 10.

Figure 9:
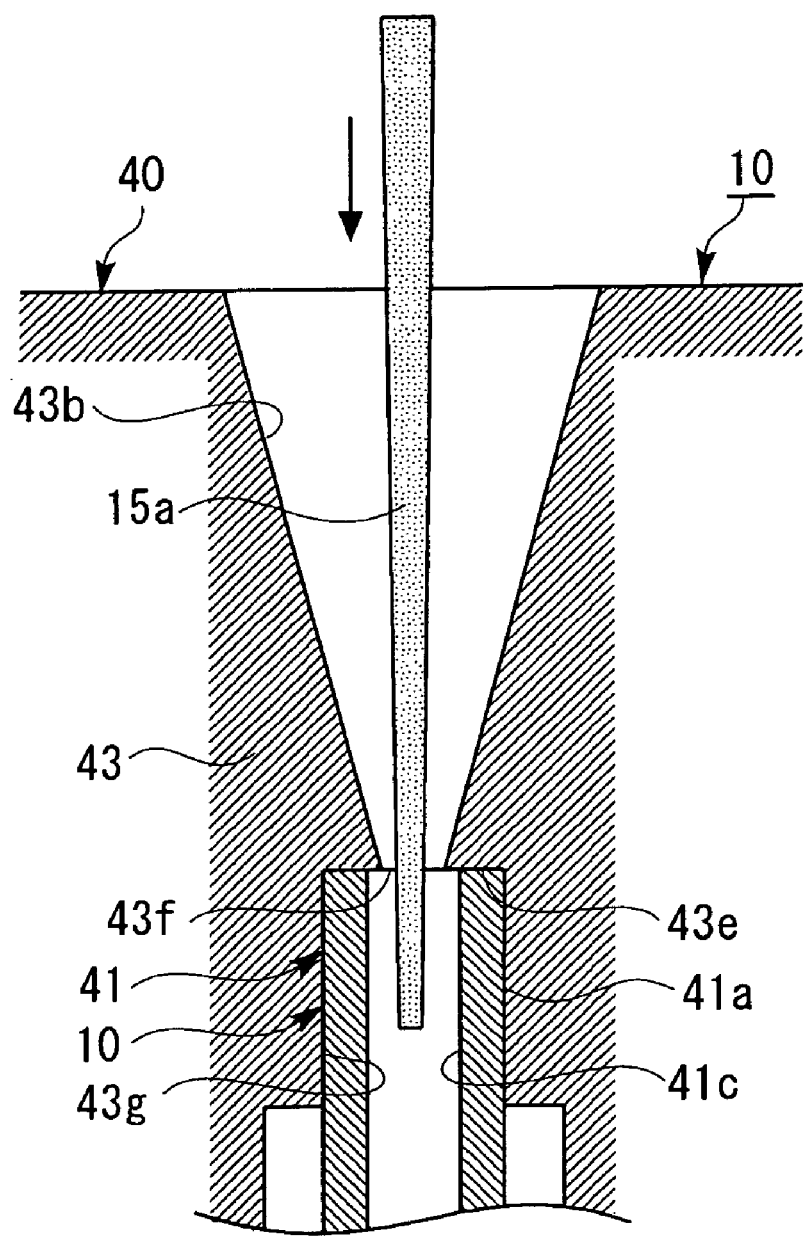
FIG. 9 is a sectional view showing a guide hole for the micro needle according to the present invention.

When introducing the introduction substance in the micro needle 10 into the introduction target micro body 13, as illustrated in FIG. 9, in a state where the micro needle 10 is grasped by the manipulator 14, a tube 15a connected to the introduction substance discharging device 15 is inserted into the proximal portion 41a of the glass tube 41 in the micro needle 10.

At this time, the tube 15a is guided along the guide hole 43b in the holder 40 for the micro needle 10 and is inserted into the glass tube 41. Further, in the present embodiment, the glass tube 41 is inserted until it is brought into contact with a bottom surface 43e of a needle insertion hole 43g of the holder 40.

The bottom surface 43e of this needle insertion hole 43g is provided on the same plane as a minimum-diameter portion 43f of the guide hole 43b. Thus, a gap is not formed between the guide hole 43b and the needle insertion hole 43g, and hence the tube 15a is surely inserted into the glass tube 41.

After the tube 15a has been inserted into the micro needle 10, the manipulator 14 manipulates the micro needle 10. Then, as shown in FIG. 1, the tip of the glass tube 41 in the micro needle 10 is inserted into the introduction target micro body 13 on a tray 17.

Next, the introduction substance discharging device 15 operates to apply the pressure to the introduction substance in the micro needle 10 through the tube 15a. With this operation, the introduction substance is discharged from the micro needle 10 and is introduced into the introduction target micro body 13. It should be noted that the introduction substance discharging device 15 can involve using a proper pressurizing device such as a small-sized air blower or compressor.

After the introduction substance in the micro needle 10 has been introduced into the introduction target micro body 13, a manipulator 14 disposed disposes the micro needle 10 in the ready-for-introducing position P2. Then, the cap 44 grasped by the micro needle transporting device 12 is attached to the micro needle 10. This micro needle 10 is ejected and then collected into a collecting container 18 by the manipulator 14.

<Processing Flow>

Figure 10:
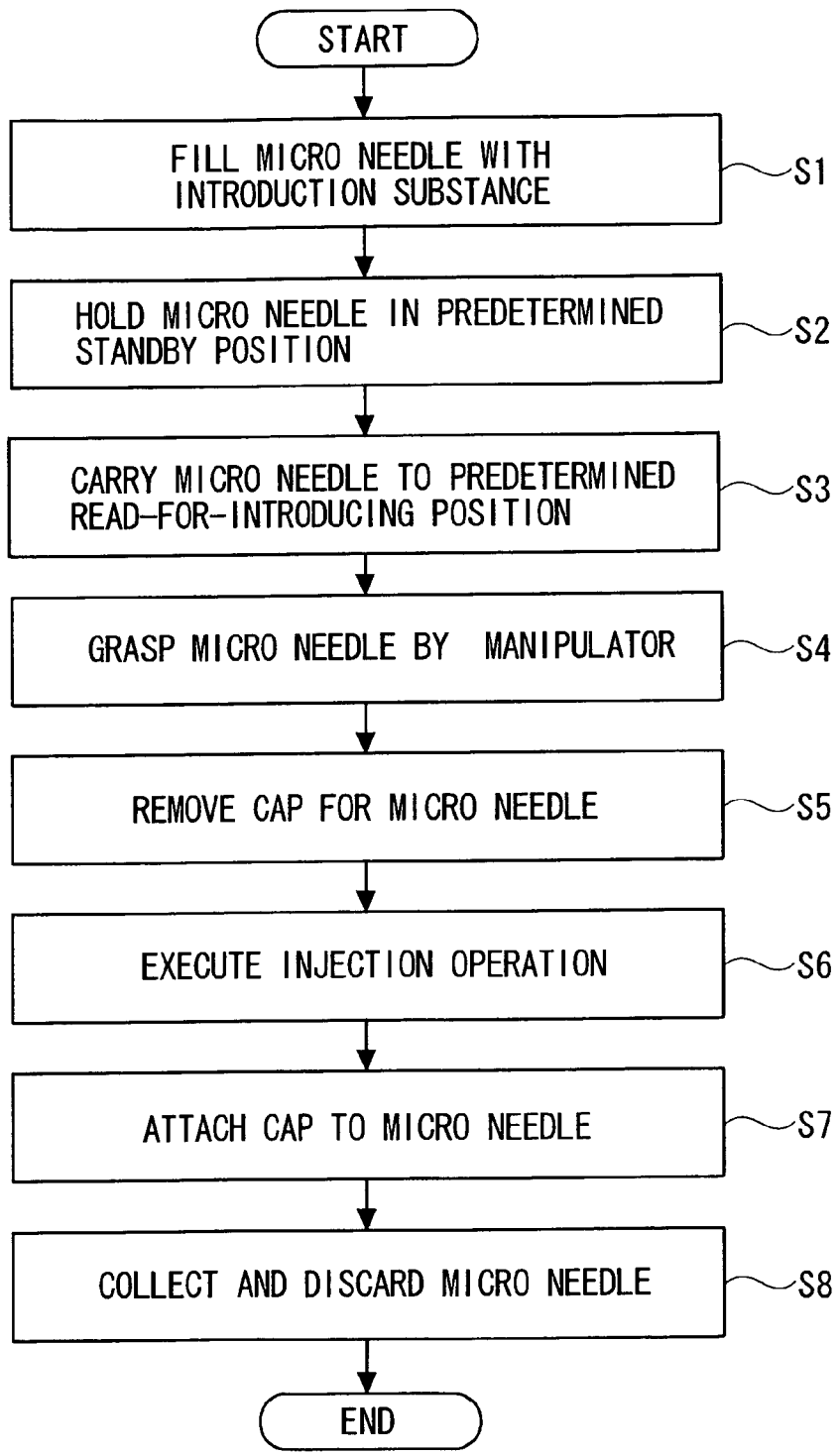
FIG. 10 is a flowchart showing a processing flow according to the present invention.

FIG. 10 shows a processing flow of the microinjection equipment 1. In this process, to start with, the introduction substance is filled into the micro needle (S1). Next, the micro needle is disposed in the predetermined standby position (S2).

Next, the micro needle is grasped by the micro needle transporting device and is disposed in the predetermined ready-for-introducing position (S3). Subsequently, the micro needle is grasped by the manipulator (S4).

Next, the cap of the micro needle is taken off (S5). Subsequently, the manipulator executes an injection operation, thereby introducing the introduction substance in the micro needle into the introduction target micro body (S6).

Next, the cap is attached to the micro needle (S7). Subsequently, the micro needle is ejected, then collected and discarded into the collecting container (S8). Thereafter, the same processes as those described above are repeatedly executed. Note that the introduction target micro body 13 is supplied manually or automatically.

Thus, the microinjection equipment 1 according to the present invention is capable of automatically fitting the micro needle 10 to the manipulator 14. It is therefore possible to conduct the operations of fitting and exchanging the micro needle 10 in a short period of time.

Further, it is feasible to automatically perform the operation of transporting the micro needle 10 filled with the introduction substance to the ready-for-introducing position from the standby position, the operation of fitting the micro needle 10 to the manipulator 14, the operation of introducing the introduction substance in the micro needle 10 into the introduction target micro body 13, and the operation of collecting the micro needle 10. Accordingly, neither the hand nor the finger touches the micro needle 10, and hence damaging and contaminating the micro needle 10 can be suppressed.

Moreover, the micro needle 10 fitted to the manipulator 14 is positioned in the direction of the central-axis line and in the orthogonal direction orthogonal to the direction of the central-axis line, and therefore, when exchanging the micro needle 10, the position of the needle tip of the micro needle 10 can be prevented from changing.

Hence, there is no necessity of adjusting the position of the micro needle 10 each time the micro needle 10 is exchanged as hitherto done, and therefore the operation efficiency can be improved.

Furthermore, according to this microinjection equipment 1, an access to each individual cell and the transportation of the micro particle such as the cell can be actualized within the same device. It is therefore feasible to introduce the substance into a large quantity of cells, while individual cells are being recognized.

It should be noted that the present embodiment has exemplified the case of including the introduction substance filling device 11. The present invention may be configured without including the introduction substance filling device 11. In this case, the micro needle 10 may be disposed in the predetermined standby position P1 manually or by a proper device.

<Others>

The disclosures of Japanese patent application NO. JP2006-184550 filed on Jul. 4, 2006 including the specification, drawings and abstract are incorporated herein by reference.

What is claimed is:

1. A microinjection equipment introducing an introduction substance, filled into an interior of a micro needle, into an introduction target micro body, comprising:
    a micro needle transporting device to grasp a cap for protecting a needle tip included in the micro needle filled with the introduction substance, and transporting the micro needle to a predetermined position;
    a micro needle inserting/removing device to grasp a holder that holds a glass tube forming the needle tip of the micro needle transported to the predetermined position, removing the holder from the cap grasped by the micro needle transporting device, and inserting and removing the tip of the micro needle into and from the introduction target micro body; and
    an introduction substance discharging device to discharge the introduction substance from the micro needle by applying a predetermined pressure to the introduction substance in the micro needle grasped by the micro needle inserting/removing device.

2. The microinjection equipment according to claim 1, further comprising a micro needle collecting device to collect the micro needle grasped by the micro needle inserting/removing device.

3. The microinjection equipment according to claim 1, wherein the micro needle inserting/removing device to grasp the holder having a first holding member that holds an intermediate portion of the glass tube and a second holding member that holds a proximal portion of the glass tube, and inserting and removing the tip of the micro needle into and from the introduction target micro body.

4. The microinjection equipment according to claim 3, wherein the introduction substance discharging device to discharge the introduction substance from the micro needle by applying the predetermined pressure to the introduction substance in the micro needle via a tube that guided into the micro needle by a guide hole provided in the holder.

5. The microinjection equipment according to claim 3, wherein the micro needle inserting/removing device has an insertion hole into which the proximal portion of the micro needle is inserted, grasps the holder such that an edge surface of the micro needle is in pressure contact with a bottom surface of the insertion hole, removes the holder from the cap grasped by the micro needle transporting device, and inserts and removes the tip of the micro needle into and from the introduction target micro body.

6. The microinjection equipment according to claim 5, wherein the micro needle inserting/removing device grasps the holder that the bottom surface of the insertion hole is provided on the same plane as a minimum diameter portion of the guide hole, removes the holder from the cap grasped by the micro needle transporting device, and inserts and removes the tip of the micro needle into and from the introduction target micro body.

7. The microinjection equipment according to claim 3, wherein the micro needle inserting/removing device grasps the holder that includes a flange portion, of which an outer peripheral surface is formed in a circular shape, protruding sideways from the outer peripheral surface thereof, removes the holder from the cap grasped by the micro needle transporting device, and inserts and removes the tip of the micro needle into and from the introduction target micro body.

8. The microinjection equipment according to claim 3, wherein the micro needle inserting/removing device includes a central-axis line directional positioning device that positions the micro needle in a direction of the central-axis line, and an orthogonal direction positioning device that positions the micro needle in a direction orthogonal to the central-axis line.

9. A microinjection equipment introducing an introduction substance, filled into an interior of a micro needle, into an introduction target micro body, comprising:
    a micro needle transporting device to grasp a cap for protecting a needle tip included in the micro needle filled with the introduction substance, and transporting the micro needle to a predetermined position;
    a micro needle inserting/removing device to grasp a holder that holds a glass tube forming the needle tip of the micro needle transported to the predetermined position, remove the holder from the cap grasped by the micro needle transporting device, and insert and remove the tip of the micro needle into and from the introduction target micro body; and
    an introduction substance discharging device to discharge the introduction substance from the micro needle by applying a predetermined pressure to the introduction substance in the micro needle grasped by the micro needle inserting/removing device,
    wherein the micro needle inserting/removing device grasps the holder having a first holding member that holds an intermediate portion of the glass tube and a second holding member that holds a proximal portion of the glass tube, and inserts and removes the tip of the micro needle into and from the introduction target micro body,
    wherein the micro needle inserting/removing device includes a central-axis line directional positioning device that positions the micro needle in a direction of the central-axis line, and an orthogonal direction positioning device that positions the micro needle in a direction orthogonal to the central-axis line, and
    wherein the central-axis line directional positioning device includes a cylinder that presses the micro needle in the direction of the central-axis line, and a support surface that supports an edge surface of a flange portion of the holder, and the orthogonal direction positioning device includes a V-groove that supports the outer peripheral surface of the holder, and a pressing device that presses the outer peripheral surface from the opposite side to the V-groove.

10. A microinjection equipment introducing an introduction substance, filled into an interior of a micro needle, into an introduction target micro body, comprising:

- a micro needle transporting device to grasp a cap for protecting a needle tip included in the micro needle filled with the introduction substance, and transporting the micro needle to a predetermined position;
- a micro needle inserting/removing device to grasp a holder that holds a glass tube forming the needle tip of the micro needle transported to the predetermined position, removes the holder from the cap grasped by the micro needle transporting device, and inserts and removes the tip of the micro needle into and from the introduction target micro body; and
- an introduction substance discharging device to discharge the introduction substance from the micro needle by applying a predetermined pressure to the introduction substance in the micro needle grasped by the micro needle inserting/removing device,
- wherein the micro needle inserting/removing device grasps the holder having a first holding member that holds an intermediate portion of the glass tube and a second holding member that holds a proximal portion of the glass tube, and inserts and removes the tip of the micro needle into and from the introduction target micro body,
- wherein the micro needle inserting/removing device includes a central-axis line directional positioning device that positions the micro needle in a direction of the central-axis line, and an orthogonal direction positioning device that positions the micro needle in a direction orthogonal to the central-axis line,
- wherein the central-axis line directional positioning device includes a cylinder that presses the micro needle in the direction of the central-axis line, and a support surface that supports an edge surface of a flange portion of the holder, and the orthogonal direction positioning device includes a V-groove that supports the outer peripheral surface of the holder, and a pressing device that presses the outer peripheral surface from the opposite side to the V-groove, and
- wherein the pressing device includes a plate member with is in pressure contact with the outer peripheral surface of the holder, a rotary shaft that rotatably supports the plate member in a direction to close to or away from the outer peripheral surface of the holder, and a cylinder that biases the plate member toward the outer peripheral surface of the holder.

* * * * *